United States Patent [19]

Cetenko et al.

[11] Patent Number: 5,112,868
[45] Date of Patent: May 12, 1992

[54] HYDROXAMATE DERIVATIVES OF SELECTED NONSTEROIDAL ANTIINFLAMMATORY ACYL RESIDUES HAVING CYCLOOXYGENASE AND 5-LIPOXYGENASE INHIBITION

[75] Inventors: Wiaczeslaw A. Cetenko; David T. Connor; Daniel L. Flynn; Jagadish C. Sircar, all of Ann Arbor, Mich.

[73] Assignee: Warner-Lambert Company, Morris Plains, N.J.

[21] Appl. No.: 518,007

[22] Filed: May 2, 1990

Related U.S. Application Data

[62] Division of Ser. No. 196,584, May 19, 1988, Pat. No. 4,943,587.

[51] Int. Cl.⁵ .............. A61K 31/38; A61K 31/40; A61K 31/495; A61K 31/165; A61K 31/18; A61K 31/325; A61K 31/34; C07D 213/72; C07C 261/04; C07C 233/81

[52] U.S. Cl. .................. 514/618; 562/442; 562/443; 562/444; 562/448; 562/449; 562/450; 562/428; 562/434; 562/435; 562/437; 564/102; 564/162; 564/163; 564/164; 564/165; 564/166; 564/167; 564/168; 564/169; 564/170; 564/172; 564/176; 564/180; 548/195; 548/337; 548/557; 548/558; 560/9; 560/10; 560/11; 560/12; 560/13; 560/16; 560/20; 560/21; 560/22; 560/23; 560/24; 560/28; 560/29; 560/30; 560/31; 560/32; 560/33; 514/255; 514/352; 514/371; 514/398; 514/426; 514/447; 514/472; 514/480; 514/561; 514/562; 514/563; 514/608; 514/617; 514/619; 514/620; 514/621; 514/622; 544/336; 546/309

[58] Field of Search ............. 564/164, 102, 162, 163, 564/165, 166, 167, 168, 169, 170, 172, 176, 180; 514/255, 352, 371, 398, 426, 447, 472, 480, 561, 562, 563, 608, 617, 618, 619, 620, 621, 622; 562/428, 434, 435, 437, 442, 443, 444, 448, 449, 450; 560/9, 10, 11, 12, 13, 16, 20, 21, 22, 23, 24, 28, 29, 30, 31, 32, 33; 549/69, 480; 548/195, 337, 557, 558; 546/309; 544/336

[56] References Cited

U.S. PATENT DOCUMENTS

| | | | |
|---|---|---|---|
| 3,624,103 | 11/1974 | DeMartlis | 260/326.13 A |
| 3,654,349 | 4/1972 | Shen et al. | 260/515 M |
| 4,029,815 | 6/1977 | Sherlock | 424/309 |
| 4,092,430 | 5/1978 | Sallmann et al. | 424/324 |
| 4,173,577 | 11/1979 | Sallmann et al. | 260/500.5 H |

FOREIGN PATENT DOCUMENTS

| | | |
|---|---|---|
| 039051 | 4/1981 | European Pat. Off. |
| 0196184 | 10/1986 | European Pat. Off. |
| 0196674 | 10/1986 | European Pat. Off. |
| 2008332 | 9/1971 | Fed. Rep. of Germany |
| 1579495 | 12/1968 | France |
| 2457867 | 11/1967 | Japan |

OTHER PUBLICATIONS

Arzneimittel Forschung Drug Research, vol. 30(II), No. 8a, Aug. 1980, pp. 1314-1325 (1980).
Poster Session—ACS Meeting New Orleans Sep. 1987.
J. Med. Chem., 1987, 30, 574-580.
J. Med. Chem., 1987, 30, 2121-2126.
Wolf, E., and Kohl, H., Ann. Chem. Liegigs, 1975, 1245-1251.

*Primary Examiner*—Johann Richter
*Attorney, Agent, or Firm*—Ronald A. Daignault

[57] ABSTRACT

The present invention is novel selected hydroxamic acid derivatives of acyl residues of selected NSAIDS, i.e. having 5-lipoxygenase and cyclooxygenase inhibiting properties, pharmaceutical compositions for treating conditions advantageously affected by the inhibition and methods for treating these conditions in mammals, including humans suffering therefor.

7 Claims, No Drawings

HYDROXAMATE DERIVATIVES OF SELECTED NONSTEROIDAL ANTIINFLAMMATORY ACYL RESIDUES HAVING CYCLOOXYGENASE AND 5-LIPOXYGENASE INHIBITION

This is a divisonal application of U.S. Ser. No. 07/196,584 filed May 19, 1988 now U.S. Pat. No. 4,943,587.

BACKGROUND OF THE INVENTION

The present invention is novel hydroxamate analogs of acyl residues of selected nonsteroidal antiinflammatory drug(s) (NSAID(S)). Such NSAIDS include indomethacin and its analogs of U.S. Pat. No. 3,161,654; sulindac and its analogs of U.S. Pat. No. 3,654,349; tolmetin and its analogs of U.S. Pat. No. 3,752,826; and furofenac and its analogs of U.S. Pat. No. 4,029,811; fentiazac and its analogs of U.S. Pat. No. 3,476,766; clidanac and its analogs of U.S. Pat. No. 3,565,943; ketorolac of U.S. Pat. No. 4,089,969; oxepinac of British Patent No. 1,476,214; fenclorac of U.S. Pat. No. 3,864,384; lonazolac of U.S. Pat. No. 4,146,721; metiazinic acid of U.S. Pat. Nos. 3,455,917 and 3,424,748; clopirac of Belgian Patent No. 777,207; clometacine of British Patent No. 1,260,868; etodolac of U.S. 3,939,178; indoprofen of British Patent No. 1,344,663; piriprofen of U.S. Pat. No. 3,641,040; carprofen of U.S. Pat. No. 3,896,145; oxaprozin of U.S. Pat. No. 3,578,671; pranoprofen of U.S. Pat. No. 3,931,205; suprofen of U.S. Pat. No. 4,035,376; miroprofen of U.S. Pat. No. 3,978,071; tioxaprofen of U.S. Pat. No. 3,933,840; furaprofen of German Patent No. DE 3026402 or furobufen of U.S. Pat. No. 3,728,349 or diclofenac of U.S. Pat. No. 3,558,690; and bucloxic acid of U.S. Pat. No. 3,754,021.

The above patents are each incorporated by reference.

Anthranilic acid derivatives of a fenamic acid series are previously known to include the generic compounds of the British Patent No. 989,951 or formula

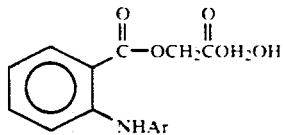

wherein Ar is α,α,α-trifluoro-m-tolyl; 2,3-xylyl, or 2,6-dichloro-m-tolyl, also in U.S. Pat. No. 3,852,333.

Of these, disclosures for unsubstituted hydroxamic acid of the acetyl residue of indomethacin are found in U.S. Pat. No. 3,624,103 and diclofenac are found in U.S. Pat. Nos. 4,092,430 and 4,173,577. However, no teaching to further substituted hydroxamic acids of indomethacin and diclofenac having the activity of the present invention compounds is found.

Among related aminobenzhydroxamic acids also previously known are compounds of the formula

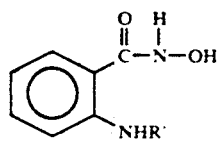

wherein R' is a saturated fatty hydrocarbon radical; phenyl, phenylalkyl, wherein the rings are optionally substituted by lower alkyl or lower alkoxy; or an aromatic heterocyclic group. This disclosure is in Japanese Application 24578/67 filed Apr. 2, 1964 by the Takeda Chemical Industry Co., Ltd. as an o-aminobenzhydroxamic acid analgesic derivative having less toxicity and analgesic, anticatarrhic, and antifebrile activity. Other related disclosures include U.S. Pat. No. 4,029,815 to compounds of the formula

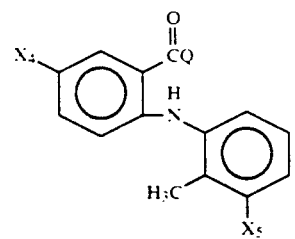

wherein $X_5$ is trifluoromethyl, difluoromethyl, or nitro, $X_4$ is H, Br, Cl, or nitro, and Q may be NHOH. These compounds have utility as antidiarrheal agents.

Selected fenamic acid derivatives having an hydroxamic acid derived substituent are found in copending U.S. application Ser. No. 134725.

Cyclized o-aminobenzhydroxamic-O-methylether of the formula

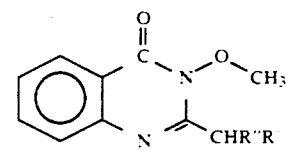

wherein R" is alkyl, aralkyl, or a basic side chain and R' is H, Cl, or Br; are disclosed by Wolf, E. and Kohl, H. in "Cyclisiarungareaktionen von am Aminostickstoff Substituierten o-Aminobenzhydroxamsaure-O-methylesteror," *Ann. Chem. Liebigs,* 1975, 1245-1251.

Wolf and Kohl also disclose an intermediate hydroxamic acid derivative from which the cyclized o-aminobenzhydroxamic-O-methylether are made. The intermediate is

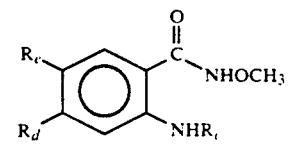

wherein $R_c$, $R_e$, and $R_d$ are as defined below.

Other cyclized o-aminobenzhydroxamic acids disclosed are

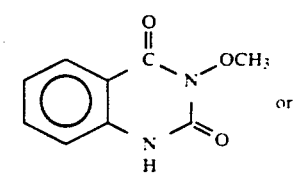

or

-continued

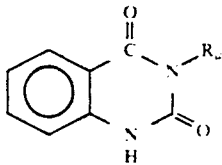

wherein $R_a$ is $CH_2CO_2C_2H_5$, $C_6H_3Cl(p)NO_2(m)$ and suggesting that $R_a$ may also be $SO_2C_6H_4CH_3(p)$; and

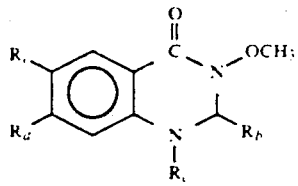

wherein $R_b$ is H or phenyl; $R_c$ is H, $CH_2C_6H_5$, $C_6H_4Cl(p)$, $CH_2C_6H_4Cl(p)$, $C_6H_5$, or $CH_3$; $R_c$ is H or $NO_2$; and $R_d$ is H or Cl. However, Wolf and Kohl do not disclose activity for these cyclized compounds and, further, do not make obvious the present invention.

Broadly, hydroxamic acid derivatives of selected aryl ring systems are disclosed in European Application Publication No. 0 196 184 and 196 674 having surprisingly high potency particularly by inhalation, oral efficacy, and with a surprisingly long duration of action. However, these aryl ring systems are in no way related to the present NSAID type compounds.

Two disclosures by Summers et al, (1) *J. Med. Chem.*, 1987, 30, 574–80 and 2121–2126 and (2) In Vivo Characterization of Hydroxamic Acid Inhibitors of 5-Lipoxygenase disclosed at a Poster session at a National ACS meeting (New Orleaans) meeting in September, 1987 (Abstract) disclose hydroxamic acids as inhibitors of 5-lipoxygenase, however, the disclosures do not extend beyond very limited representative examples not including any derivatives having the selected acyl residues of the present invention.

Thus, the present invention are to selected novel derivatives of NSAIDS and pharmaceutically acceptable acid addition or base salts thereof, pharmaceutical compositions for treating allergy, psoriasis, inflammation, arthritis, pain, pyrrhia, and the methods for such treatment.

SUMMARY OF THE INVENTION

The present invention is a novel compound of the formula (I)

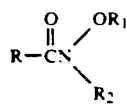    1 and pharmaceutically acceptable acid addition and base salts thereof; wherein (i)

is an acyl residue of selected NSAIDS;
(ii) $R_1$ is hydrogen, lower alkyl, or acyl; and (iii) $R_2$ is H, lower alkyl, cycloalkyl of from three to twelve carbon atoms of which from three to seven are ring carbons, aryl, aralkyl or heteroaryl with the overall proviso that when the acyl residue is of the formula

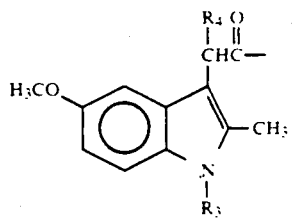

wherein $R_4$ is hydrogen or lower alkyl, then $R_3$ is hydrogen, phenylmethyl, allyl, vinyl, isopropenyl, benzoyl, chlorobenzoyl, methoxybenzoyl, and thiomethylbenzoyl; and when the acyl residue is of the formula

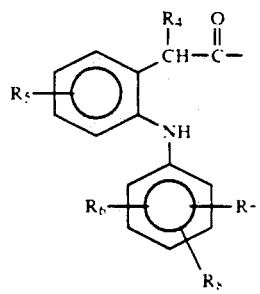

wherein $R_5$, $R_6$, $R_7$ and $R_8$ are independently H, chlorine, fluorine, or bromine, lower alkyl, lower alkoxy, or trifluoromethyl but when $R_4$ is hydrogen then are not all hydrogen; and $R_4$ is otherwise independently as defined above; then $R_1$ and $R_2$ cannot both be hydrogen.

The present invention is also a pharmaceutical composition for the treatment of conditions advantageously affected by the inhibition of 5-lipoxygenase and/or cyclooxygenase which comprises administering an amount effective for inhibiting 5-lipoxygenase and/or cyclooxygenase of a novel compound of the formula I as defined above; and a pharmaceutically acceptable carrier.

Further, the present invention also provides a method of use for a composition of a compound of the formula I, as defined hereinbefore, or physiologically acceptable acid addition or base salt thereof for use to treat a condition which is advantageously affected by the inhibition of the lipoxygenase and cyclooxygenase enzymes of the mammalian, including human, arachidonic acid metabolism, which method comprises inhibition of such enzymes by administration to a mammal of a lipoxygenase and cyclooxygenase inhibiting amount of any such compound or salt in unit dosage form, and to use of any such compound or salt in the manufacture of lipoxygenase and/or cyclooxygenase inhibitor agents.

Further, the present invention also provides any compound or composition of the formula I' or physiologically acceptable salt thereof, for use as a medical therapeutic or prophylactic agent, to methods of medical therapeutic or prophylactic treatment by administration to a mammal of a medically therapeutic or prophylactic effective amount of any such compound or salt, and to use of any such compound or salt in the manufacture of medical therapeutic or prophylactic agents. The kinds of medical therapy and prophylaxis pertinent to the foregoing and therefore in that sense comprising part of the present invention, are elaborated by way of example in the following paragraphs which are not intended to be construed as in any way limiting the scope of these aspects of said invention.

DETAILED DESCRIPTION OF THE INVENTION

In the compounds of formula I the term "lower alkyl" is meant to include a straight or branched alkyl group having one to six carbon atoms, such as, for example, methyl, ethyl, propyl, butyl, pentyl or hexyl and isomers thereof.

Lower alkoxy is O-alkyl or of from one to four carbon atoms as defined above for "lower alkyl".

Acyl is a

lower alkyl or

phenyl optionally substituted by a lower alkyl, fluoro, chloro, bromo, trifluoromethyl, hydroxy, or lower alkoxy; and wherein the lower alkyl is as defined above.

Cycloalkyl of from three to ten carbons having from three to seven ring carbons includes cyclopropyl, cyclobutyl, methylcyclotrityl, ethylcyclobutyl, dimethylcyclobutyl, cyclopentyl, and the like.

Aryl or aromatic radical is phenyl unsubstituted and substituted with from one to three substituents selected from the group consisting of hydroxy, lower alkoxy, fluoro, chloro, bromo, trifluoromethyl, lower alkyl, CN, —S(O)$_n$-lower alkyl wherein n is as defined above, NO$_2$, or NR$_9$R$_{10}$ wherein R$_9$ and R$_{10}$ are independently hydrogen or lower alkyl.

An aralkyl is an aryl as defined above attached through a lower alkylenyl wherein the alkylenyl, straight or branched chain, is of from one to four carbons such as methylenyl, 1,2-ethylenyl, 1,1-ethylenyl, propylenyl, and the like.

Heterocycles includes derivatives of furan, thiophene, pyrrole, piperidine, dihydrofuran, pyridine, thiazole, piperazine, oxazole, benzofuran, tetrahydroquinoline, quinoline, indole, dihydroindole, benzothiophene, dihydrobenzothiophene, benzoxazole, and similar heterocyclic rings.

The cycloalkyl and fused cycloalkyl groups may be mono or polycyclic and contain from three to twenty carbons. These groups include cyclopropyl, cyclopentyl, cyclohexyl, cycloheptyl, bornyl, norbornyl, indanyl and the like which are optionally substituted by lower alkyl up to a total of twelve carbons.

Physiologically acceptable salts are meant to be synonymous with pharmacologically acceptable salts in this invention.

An acyl residue of selected NSAIDS is RCO of the formula

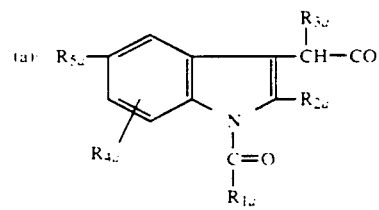

in which

R$_{1a}$ is selected from the group consisting of benzene, naphthalene, biphenyl and substituted benzene, naphthalene and biphenyl radicals in which said substituent is selected from the group consisting of halogen, lower alkyl, lower alkylthio, lower alkoxy, trifluoromethyl, phenoxy, lower alkyl phenoxy, lower alkoxy phenoxy, halogenophenoxy, trifluoroacetyl, difluoroacetyl, monofluoroacetyl, di-lower alkyl sulfamyl, lower alkanoyl, di-lower alkyl carboxamido, cyano, carb-lower alkoxy, trifluoromethylthio, lower alkyl sulfinyl, lower alkylsulfonyl, benzylthio, lower alkylbenzylthio, lower alkoxybenzylthio, halogenobenzylthio, mercapto, nitro, amino, di-(lower alkyl)amino, lower alkylamino, lower alkanoylamino, hydroxy, lower alkanoyloxy, trifluoroacetoxy, difluoroacetoxy, monofluoroacetoxy, benzyloxy, lower alkylbenzyloxy, lower alkoxylbenzyloxy, and halogenobenzyloxy;

R$_{2a}$ is selected from the group consisting of hydrogen, lower alkenyl and lower alkyl;

R$_{3a}$ is selected from the group consisting of hydrogen and lower alkyl;

R$_{4a}$ is selected from the group consisting of hydrogen, lower alkyl, lower alkoxy, fluorine and trifluoromethyl;

R$_{5a}$ is selected from the group consisting of hydrogen, hydroxy, lower alkyl, lower alkoxy, nitro, amino, lower alkylamino, di(lower alkyl) amino, lower alkanoylamino, lower alkanoyl, lower alkylamino, bis(hydroxy lower alkyl)amino, 1-pyrrolidino, 4-methyl-1-piperizinyl, 4-morpholinyl, cyano, amino lower alkyl, di-lower alkyl amino, lower alkyl, trifluoromethyl, halogen, di(lower alkyl)sulfamyl, benzylthio, lower alkylbenzylthio, lower alkoxybenzylthio, halogenobenzylthio, benzyloxy, lower alkylbenzyloxy, lower alkoxybenzyloxy, halogenobenzyloxy, lower alkenyl, lower alkenyloxy, 1-azacyclopropyl, cyclopropyl(lower alkoxy) methyoxy, and cyclobutyl(lower alkoxy)-methyoxy.

(The most preferred compound of the present invention is the compound of formula I$_a$ wherein RCO is the acyl residue of 1-(4-chlorobenzoyl)-2-methyl-5-methoxy-3-indole acetic acid.)

(b) 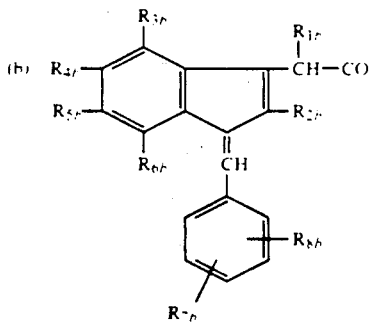

wherein:
- $R_{1h}$ is hydrogen, lower alkyl or halogenated lower alkyl;
- $R_{2h}$ is hydrogen or alkyl;
- $R_{3h}$, $R_{4h}$, $R_{5h}$ and $R_{6h}$ each are hydrogen, lower alkyl, lower alkoxy, nitro, amino, lower alkylamino, lower dialkylamino, lower dialkylamino lower alkyl, sulfamyl, lower alkylthio, mercapto, hydroxy, hydroxy lower alkyl, lower alkylsulfonyl, halogen, carboxyl, carbo-lower alkoxy, carbamido, halogenoalkyl, cycloalkyl, or cycloalkoxy;
- $R_{7h}$ is lower alkylthio, alkylsulfinyl or alkylsulfonyl;
- $R_{8h}$ is hydrogen, halogen, hydroxy, alkoxy or haloalkyl.

(The most preferred compound of the formula I wherein RCO is defined in group (b) is the compound wherein RCO is $I_h$ wherein $R_{1h}$ is hydrogen; $R_{2h}$ is methyl; $R_{3h}$ is hydrogen; $R_{4h}$ is fluoro; $R_{5h}$ is hydrogen; $R_{6h}$ is hydrogen; $R_{7h}$ is p-methylsulfinyl; and $R_{8h}$ is hydrogen.

(c) 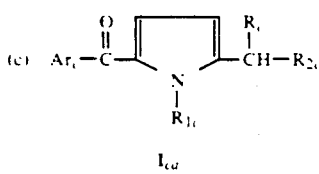

$I_{ca}$

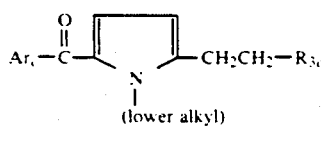

$I_{cb}$

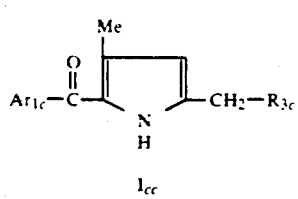

$I_{cc}$

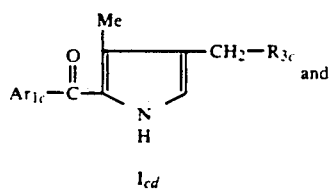

$I_{cd}$ $I_h$ 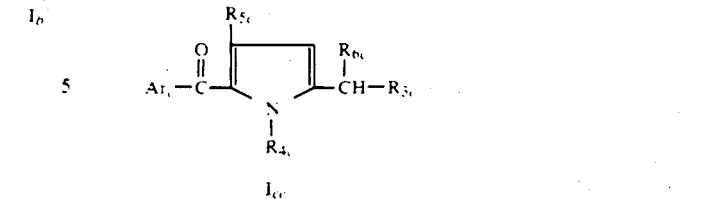

$I_{ce}$ wherein:
- $Ar_c$ represents a member selected from the group consisting of phenyl, thienyl, 5-methylthienyl, monosubstituted phenyl, disubstituted phenyl and trisubstituted phenyl, each substituent of said substituted phenyls being a member selected from the group consisting of halo, lower alkyl, trifluoromethyl, lower alkoxy, nitro, amino, methylthio and cyano;
- $Ar_{1c}$ represents a member selected from the group consisting of phenyl, monosubstituted phenyl, disubstituted phenyl and trisubstituted phenyl, each substituent of said substituted phenyls being a member selected from the group consisting of halo, lower alkyl and lower alkoxy;
- $R_c$ represents a member selected from the group consisting of hydrogen and lower alkyl;
- $R_{1c}$ represents a member selected from the group consisting of hydrogen, lower alkyl and benzyl;
- $R_{2c}$ represents

- $R_{3c}$ represents

- $R_{4c}$ represents lower alkyl;
- $R_{5c}$ represents lower alkyl; and
- $R_{6c}$ represents a member selected from the group consisting of hydrogen and lower alkyl.

(The most preferred compound of the formula I wherein RCO is defined in group (c) is the compound wherein RCO is the acyl residue of 5-(4-methylbenzoyl)-1-methylpyrrolo-2-acetic acid.)

(d) $R_d-CH_2-\overset{O}{\underset{\|}{C}}$  $\quad I_d$ wherein $R_d$ represents a group selected from:

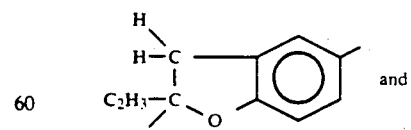 and

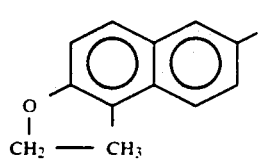

(e)

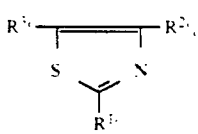

wherein $R^{1e}$ and $R^{2e}$ are each radicals of the group consisting of thienyl, furyl, naphthyl, phenyl, and phenyl bearing from one to two substituents of the group consisting of (lower)alkyl, (lower)alkoxy, chloro, bromo, fluoro, di-(lower alkyl)amino, nitro, amino and trifluoromethyl, and wherein $R^{3e}$ is a radical from the group consisting of $-CH_2-CO$, $-CH_2-CH_2-CO$, and $-CH(CH_3)-CO$.

(The most preferred compound of the formula I wherein RCO is defined in group (e) is the compound wherein RCO is $I_e$ wherein $R^{1e}$ is phenyl, $R^{3e}$ is $-CH_2CO-$ and $R^{2e}$ is p-chlorophenyl.)

(f)

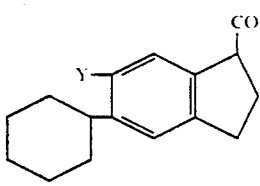

wherein Y is hydrogen, chloro, bromo, fluoro, hydroxy, (lower)alkyl, (lower)alkoxy, mercapto, cyano, nitro, amino or (lower)alkylthio.

(The most preferred compound of the formula I wherein RCO is defined in group (f) is the compound wherein RCO is the acyl residue of ($\pm$)-6-chloro-5-cyclohexyl-1-indancarboxylic acid.)

(g)

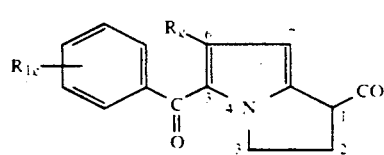

wherein $R_g$ represents hydrogen or a lower alkyl group having from one to four carbon atoms and $R_{1g}$ represents hydrogen, a lower alkyl group having from one to 4 carbon atoms, a lower alkoxy group having from one to four carbon atoms, chloro, fluoro or bromo, the $R_{1g}$ substitution being at the ortho, meta or para positions of the aroyl group.

(The most preferred compound of the formula I wherein RCO is defined in group (g) is the compound wherein RCO is the acyl residue of 5-benzoyl-1,2-dihydro-3H-pyrrolo-[1,2-a]pyrrole-1-carboxylic acid.)

(h)

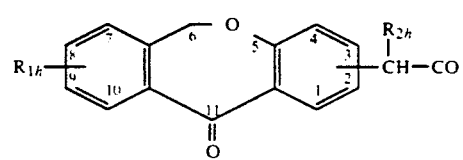

wherein $R_{1h}$ represents a hydrogen or halogen atom or a trihalomethyl or lower alkoxy group; $R_{2h}$ represents a hydrogen atom or a lower alkyl group:

(i)

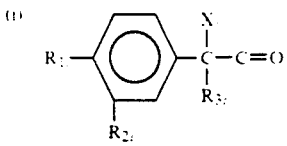

wherein $R_{1i}$ is a member selected from the group consisting of cycloalkyl with five to seven carbon atoms and lower alkyl substituted cycloalkyl;

$R_{2i}$ is a member selected from the group consisting of halogen, nitro, cyano, trifluoromethyl and lower alkylsulfonyl;

$R_{3i}$ is hydrogen;

$X_i$ is halogen.

(The most preferred compound of the formula I wherein RCO is defined in group (i) is the compound wherein RCO is the acyl residue of α,m-dichloro-p-cyclohexylphenylacetic acid.)

(j)

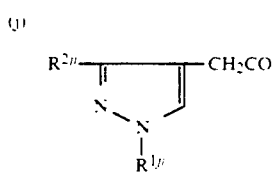

wherein $R^{1ji}$ and $R^{2ji}$ are selected from the group consisting of phenyl, halophenyl, lower alkylphenyl, dimethylphenyl, lower alkoxyphenyl, dimethoxyphenyl, lower alkylmercaptophenyl, trifluoromethylphenyl, furyl, thienyl, and naphthyl with the proviso that at least one of $R^{1ji}$ and $R^{2ji}$ is phenyl or substituted phenyl;

$I_{jii}$

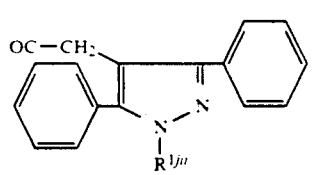

wherein $R^{1jii}$ is hydrogen, lower alkyl, phenyl, phenyl monosubstituted with lower alkyl, lower alkoxy or halogen, naphthyl, benzyl or benzyl wherein the phenyl ring thereof is monosubstituted with lower alkoxy or halogen;

$I_{jiii}$

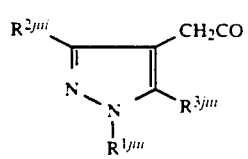

wherein $R^{1jiii}$ is phenyl; $R^{2jiii}$ is phenyl, p-halogenophenyl, p-methylphenyl or furyl; $R^{3jiii}$ is hydrogen, phenyl, or furyl; or

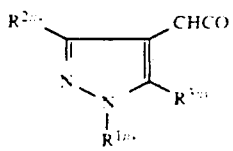

wherein R$^{1m}$ is phenyl, R$^{2m}$ is phenyl, p-halogenophenyl, p-methylphenyl, R$^{3m}$ is hydrogen or phenyl.

(The most preferred compound of the formula I wherein RCO is defined in group (j) is the compound wherein RCO is the acyl residue of 1-phenyl-3-(p-chlorophenyl)pyrazol-4-yl-acetic acid.)

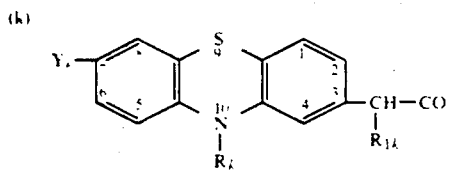

wherein $R_k$ represents hydrogen or methyl, $R_{1k}$ represents hydrogen, methyl or ethyl, and $Y_k$ represents hydrogen, halogen, or alkyl or alkoxy of 1 through 4 carbon atoms.

(The preferred compounds of the formula I wherein RCO is defined in group (k) is the compound having $I_k$ wherein $R_k$ is hydrogen or methyl, $R_{1k}$ is hydrogen, methyl or ethyl and $Y_k$ is hydrogen or methoxy, and the most preferred is the compound having $I_k$ wherein $R_k$ is methyl, $R_{1k}$ is hydrogen and $Y_k$ is hydrogen.)

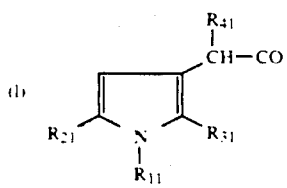

wherein $R_{11}$ is a lower alkyl or lower alkyl substituted by cycloalkyl of from three to 12 carbons having from three to seven ring carbons, lower alkenylenyl, lower alkynylenyl, aryl, benzoyl, benzoyl substituted by halogen, lower alkyl, lower alkoxy or heterocycle, such as morpholinyl piperidinyl, furanyl, and thiophenyl; $R_{2l}$ and $R_{3l}$ are the same or different and are lower alkyl, aryl and $R_{4l}$ is hydrogen or lower alkyl.

(The most preferred compound of the formula I wherein RCO is defined in group (l) is the compound wherein RCO is the group $I_l$ wherein $R_{2l}$ and $R_{3l}$ are CH$_3$, $R_{4l}$ is hydrogen and $R_{11}$ is p-chlorophenyl.)

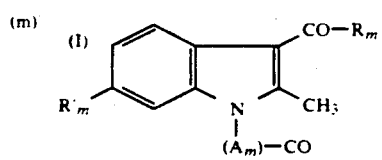

[in which A$_m$ represents a lower straight chain or branched alkylene group;

R$_m$ represents a cyclohexyl or aromatic radical;

R$_m$' represents a halogen atom, trifluoromethyl radical, an alkoxy or alkyl radical containing 1 to 4 carbon atoms or a N,N-dialkylamino radical wherein each of the alkyl groups contain 1 to 4 carbon atoms] as well as alkyl esters thereof (in which the alkyl group in the alcoholic moiety contains 1 to 4 carbon atoms).

(The most preferred compound of the formula I wherein RCO is defined in group (m) is the compound wherein RCO is the group $I_m$ wherein R$_m$ is methoxy, A$_{m}$ is —CH$_2$—, and R$_m$' is p-chlorophenyl.)

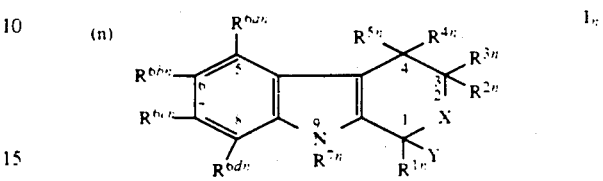

in which R$^{1n}$ is selected from the group consisting of lower alkyl, lower alkenyl, lower alkynyl, lower cycloalkyl, phenyl, benzyl and 2-thienyl. R$^{2n}$, R$^{3n}$, R$^{4n}$ and R$^{5n}$ are the same or different and are each selected from the group consisting of hydrogen and lower alkyl. R$^{6an}$, R$^{6bn}$, R$^{6cn}$, and R$^{6dn}$ are the same or different and selected from the group consisting of hydrogen, lower alkyl, hydroxy, lower alkoxy, benzyloxy, lower alkanoyloxy, nitro, halo, mercapto, lower alkylthio, trifluoromethyl, amino and sulfamoyl. R$^{7n}$ is selected from the group consisting of hydrogen, lower alkyl and lower alkenyl. X is selected from the group consisting of oxy and thio. Y is selected from the group consisting of carbonyl.

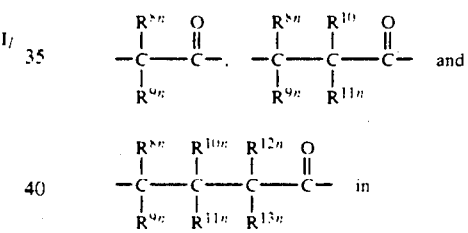

which each of R$^{8n}$, R$^{9n}$, R$^{10n}$, R$^{11n}$, R$^{12n}$ and R$^{13n}$ is hydrogen or lower alkyl.

(The most preferred compound of the formula I wherein RCO is defined in group (n) is the compound wherein RCO is the acyl residue of 1,8-diethyl-1,3,4,9-tetrahydropyrano[3,4-b]indole-1-acetic acid.)

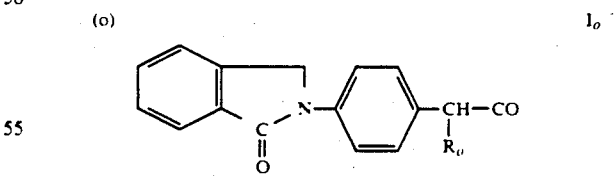

wherein R$_o$ is hydrogen or lower alkyl.

(The preferred compounds of the formula I wherein RCO is defined in group (o) is the compound I$_o$ wherein R$_o$ is CH$_3$.)

(p)  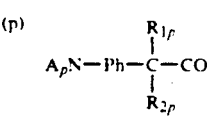  $I_p$ in which $R_{1f}$ is hydrogen or lower alkyl; $R_{2f}$ is hydrogen, alkyl, alkenyl three or four ring-membered cycloalkyl, cycloalkenyl or cycloalkyl-methyl cycloalkenyl-methyl; Ph is (i) 1,3- or 1,4-phenylene, (ii) (lower alkyl)-1,3- or 1,4-phenylene, (iii) (lower alkoxy)-1,3- or 1,4-phenylene, (iv) mono- or di-(halogeno)-1,3- or 1,4-phenylene, (v) 1,4-phenylene, (vii) (amino)-1,3- or 1,4-phenylene, (viii) (di-lower alkylamino)-1,3— or 1,4-phenylene; and

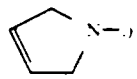

is monocyclic five to seven ring-membered lower alkyleneamino, piperazino, morpholino, thiamorpholino or N-(lower alkyl, hydroxy, lower alkyl, HPh-lower alkyl or HPh) piperazino;

(The most preferred compound of the formula I wherein the RCO is defined in group $I_f$ wherein one of $R_{1f}$ is hydrogen and the $R_{2f}$ is methyl, Ph is -1,4-(3-chlorophenylene) and $A_fN$— is

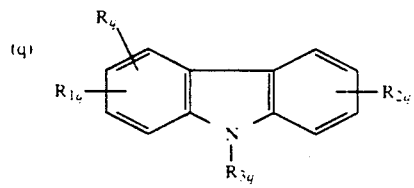

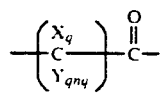

wherein $R_q$ is hydrogen, halogen, hydroxy, cyano, lower alkyl, hydroxy-lower alkyl, lower alkoxy, acetyl, benzyloxy, lower alkylthio, trifluoromethyl, carboxy, carbo-lower alkoxy, nitro, amino, mono-lower alkylamino, di-lower alkylamino, sulfamoyl, di-lower alkylsulfamoyl or difluoromethylsulfonyl; $R_{1q}$ is halogen, cyano, hydroxy-lower alkyl, lower alkoxy, acetyl, acetamido, benzyloxy, lower alkylthio, trifluoromethyl, hydroxy, carboxy, carbo-lower alkoxy, nitro, amino, mono-lower alkylamino, di-lower alkylamino, sulfamoyl, di-lower alkylsulfamoyl or difluoromethylsulfonyl; or $R_q$ taken together with an adjacent $R_{1q}$ is also lower alkylenedioxy; $R_{2q}$ is $$-\left(\begin{array}{c}X_q\\ \vert\\ C\\ \vert\\ Y_{qn_q}\end{array}\right)_{n_q}\overset{O}{\underset{\Vert}{C}}-$$

wherein $Y_q$ and $X_q$, independently, are hydrogen or lower alkyl, and nq is one to seven and $R_{3q}$ is hydrogen, lower alkyl, lower alkoxycarbonyl-lower alkyl, carboxy-lower alkyl, lower alkanoyl, halo-substituted lower alkanoyl, benzyl, halo-benzyl, benzoyl or halo-benzoyl; and when $X_q$ and $Y_q$ are different, their enantiomers.

(The more preferred compounds of the formula I wherein RCO is defined by the group (q) is the compound wherein RCO is the acyl residue of racemic 6-chloro-α-methylcarbazole-2-acetic acid.)

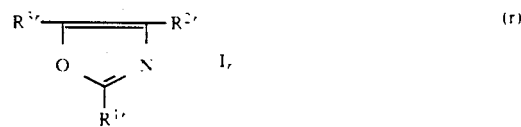

wherein each of the substituents $R^{2r}$ and $R^{3r}$ is a member of the group consisting of unsubstituted phenyl, naphthyl, thienyl and furyl radicals and phenyl radicals substituted by a substituent selected from the group consisting of halogen, lower alkyl, lower alkoxy, nitro and trifluoromethyl radicals; and wherein $R^{1r}$ is selected from the group consisting of carboxyalkyl- and carboxyalkenyl radicals each containing from two to five carbons.

(The most preferred compound of the formula I wherein RCO is defined by the group (r) is the compound wherein RCO is the acyl residue of β-(4,5-diphenyloxazol-2-yl)propionic acid.)

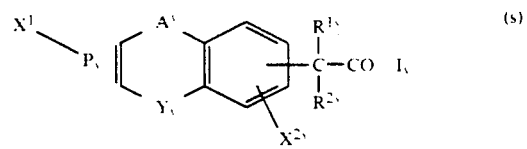

wherein each of $X^{1s}$ and $X^{2s}$ is a hydrogen atom, a halogen atom, an alkyl group having one to four carbon atoms or an alkoxy group having one to four carbon atoms; each of $R^{1s}$ and $R^{2s}$ is a hydrogen atom or an alkyl group having one to four carbon atoms; $A^s$ is carbonyl, methylene or alkylidene having two to four carbon atoms; $Y_s$ is —O—; and ring $P_s$ represents a pyridine or pyridine N-oxide ring.

(The most preferred compound of the formula I wherein RCO is defined by the group (s) is the compound wherein RCO is the acyl residue of 2-(5H-[1]benzopyrano[2,3-b]pyridin-7-yl)propionic acid.)

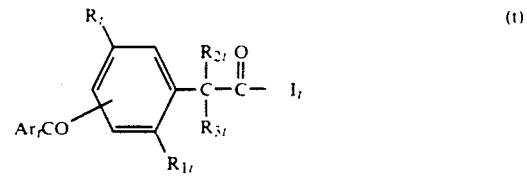

wherein:
Ar$_t$CO is an aroyl substituent the Ar$_t$ function of which is a member selected from the group consisting of 2-thienyl, 5-lower alkyl-2-thienyl, 5-halo-2-thienyl, 2-naphthyl and 3-pyridyl, said Ar$_t$CO being in the meta- or para-position relative to the acetyl function;
either of R$_t$ and R$_{1t}$ is hydrogen, the other being a member selected from the group consisting of hydrogen, halo and lower alkyl, provided that, when said R$_t$ is halo or lower alkyl, then said Ar$_t$CO is in the aforementioned para-position, and when said R$_{1t}$ is halo or lower alkyl, then said Ar$_t$CO is in the aforementioned meta-position, and further provided that when said R$_t$ or R$_{1t}$ is halo, then said Ar$_t$ is a member selected from the group consisting of 2-thienyl, 5-lower alkyl-2-thienyl and 5-halo-2thienyl;

either of $R_{2i}$ and $R_{3i}$ is a member selected from the group consisting of hydrogen, allyl and lower alkyl, the other being a member selected from the group consisting of hydrogen and lower alkyl, provided that, when either of said $R_{2i}$ and $R_{3i}$ is allyl, the other is hydrogen, and when either of said $R_{2i}$ and $R_{3i}$ is lower alkyl, the other is a member selected from the group consisting of hydrogen and lower alkyl;

$R_{2i}$ and $R_{3i}$ taken together, is an alkylene bridge attached to the α-carbon of the acetic acid function:

$$(CH_2)_{n_I}$$

$$-C-$$

wherein $n_I$ is an integer from two to five; and wherein lower alkyl as above employed is a radical having from one to five carbon atoms;

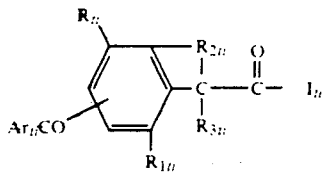

wherein $Ar_{ii}CO$ is an aroyl substituent the $Ar_{ii}$ function of which is a member selected from the group consisting of 2-thienyl, 5-methyl-2-thienyl, 5-chloro-2-thienyl, 2-naphthyl and 3-pyridyl, said $Ar_{ii}CO$ being in the meta- or para-position relative to the acetic acid function;

either of $R_{ii}$ and $R_{1ii}$ is hydrogen, the other being a member selected form the group consisting of hydrogen, chloro and methyl, provided that, when said $R_{ii}$ is chloro or methyl, then said $Ar_{ii}CO$ is in the aforementioned para-position, and when said $R_{1ii}$ is chloro or methyl, then said $Ar_{ii}CO$ is in the aforementioned meta-position, and further provided that, when said $R_{ii}$ and $R_{1ii}$ is chloro, then said $Ar_{ii}$ is a member selected from the group consisting of 2-thienyl, 5-methyl-2-thienyl and 5-chloro-2-thienyl;

either of $R_{2ii}$ and $R_{3ii}$ is a member selected from the group consisting of hydrogen, allyl and lower alkyl, the other being a member selected from the group consisting of hydrogen and lower alkyl, provided that, when either of said $R_{2ii}$ and $R_{3ii}$ is allyl, the other is hydrogen, and when either of said $R_{2ii}$ and $R_{3ii}$ is lower alkyl, the other is a member selected from the group consisting of hydrogen and lower alkyl;

$R_{2ii}$ and $R_{3ii}$, taken together, is an alkylene bridge attached to the α-carbon of the acetic acid function:

$$(CH_2)_{n_{ii}}$$

$$-C-$$

wherein $n_{ii}$ is an integer from two to five; and wherein lower alkyl as above employed is a radical having from one to five carbons;

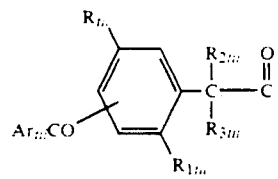

wherein:

$Ar_{iii}CO$ is an aroyl substituent the $Ar_{iii}$ function of which is a member selected from the group consisting of 2-thienyl, 5-lower alkyl-2-thienyl and 5-halo-2-thienyl, said $Ar_{iii}CO$ being in the meta- or para-position relative to the acetic acid function;

either of $R_{iii}$ and $R_{1iii}$ is hydrogen, the other being a member selected from the group consisting of hydrogen, halo and lower alkyl, provided that, when said $R_{iii}$ is halo or lower alkyl, then said $Ar_{iii}CO$ is in the aforementioned para-position, and when said $R_{1iii}$ is halo or lower alkyl, then said $Ar_{iii}CO$ is in the aforementioned meta-position;

either of $R_{2iii}$ and $R_{3iii}$ is a member selected from the group consisting of hydrogen, allyl and lower alkyl, the other being a member selected from the group consisting of hydrogen and lower alkyl, provided that, when either of said $R_{2iii}$ and $R_{3iii}$ is allyl, the other is hydrogen, and when said $R_{2iii}$ and $R_{3iii}$ is lower alkyl, the other is a member selected from the group consisting of hydrogen and lower alkyl;

$R_{2iii}$ and $R_{3iii}$ together is also an alkylene bridge with the α-carbon of the acetic acid function:

$$(CH_2)_{n_{iii}}$$

$$-C-$$

wherein $n_{iii}$ is an integer from two to five; and wherein lower alkyl as above employed is a radical having from one to five carbon atoms; or

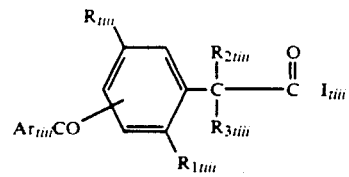

wherein:

$Ar_{iiii}CO$ is an aroyl substituent the $Ar_{iiii}$ function of which is a member selected from the group consisting of 2-thienyl, 5-methyl-2-thienyl and 5-chloro-2-thienyl, said $Ar_{iiii}CO$ being in the meta- or para-position relative to the acetic acid function;

either of $R_{iiii}$ and $R_{1iiii}$ is hydrogen, the other being a member selected from the group consisting of hydrogen, chloro and methyl, provided that, when said $R_{iiii}$ is chloro or methyl, then said $Ar_{iiii}CO$ is in the aforementioned para-position, and when said $R_{1iiii}$ is chloro or methyl, then said $Ar_{iiii}CO$ is in the aforementioned meta-position;

either of $R_{2tii}$ and $R_{3tii}$ is a member selected from the group consisting of hydrogen, allyl and lower alkyl, the other being a member selected from the group consisting of hydrogen and lower alkyl, provided that, when either of said $R_{2tii}$ and $R_{3tii}$ is allyl, the other is hydrogen, and when either of said $R_{2tii}$ and $R_{3tii}$ is lower alkyl, the other is a member selected from the group consisting of hydrogen and lower alkyl;

$R_{2tii}$ and $R_{3tii}$ together is also an alkylene bridge with the α-carbon of the acetic acid function:

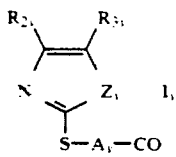

wherein $n_{tii}$ is an integer from two to five; and wherein lower alkyl as above employed is a radical having from one to five carbon atoms.

(The most preferred compound of the formula I wherein RCO is defined by the group (t) is that of $I_{ti}$ wherein $Ar_t$ is 2-thienyl, $R_{ti}$ and $R_{1ti}$ are hydrogen, $R_{2ti}$ is hydrogen and $R_{3ti}$ is methyl.)

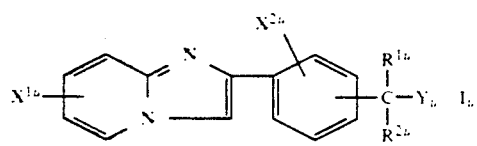 (u)

wherein each of $R^{1u}$ and $R^{2u}$ is a hydrogen atom or an alkyl group having one to four carbon atoms; each of $X^{1u}$ and $X^{2u}$ is a hydrogen atom, a halogen atom, an alkyl group having one to four carbon atoms or an alkoxy group having one to four carbon atoms; and $Y_u$ is CO.

(The most preferred compound of the formula I wherein RCO is defined by the group (u) is that wherein $X^{1u}$ and $X^{2u}$ is hydrogen, $R^{1u}$ is hydrogen and $R^{2u}$ is methyl.)

 (v)

wherein $R_{2v}$ and $R_{3v}$ each are phenyl or phenyl mono- or di-substituted by at least one member selected from the group consisting of alkyl, alkoxy, alkylmercapto, monoalkylamino, dialkylamino or alkanoylamino wherein the alkyl, alkoxy and alkanoyl each are of up to four carbon atoms, F, Cl, Br, I, $CF_3$, OH, methylenedioxy, $NH_2$ and $NO_2$, $A_v$ is $C_{na}H_{2na}$ wherein na is an integer from one to ten inclusive or

and $Z_v$ is O or S.

(The most preferred compound of the formula I wherein RCO is defined by the group $I_v$ wherein $Z_v$ is oxygen, $A_v$ is

and $R_{2v}$ and $R_{3v}$ are each parachlorophenyl.)

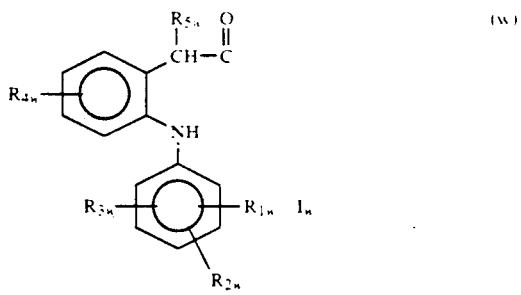 (w)

wherein $R_{1w}$, $R_{2w}$, $R_{3w}$ and $R_{4w}$ are independently hydrogen, chlorine, fluorine, bromine, lower alkyl, lower alkoxy and $R_{2w}$ may additionally be trifluoromethyl, and $R_{5w}$ is H or lower alkyl with exclusion of $R_{1w}$, $R_{2w}$ and $R_{3w}$ as hydrogen simultaneously.

(The most preferred compound of the formula I wherein RCO is defined by the group (w) is that wherein $R_{4w}$, $R_{2w}$ and $R_{5w}$ are hydrogen and $R_{3w}$ and $R_{1w}$ are each ortho-chloro.)

(x) the acyl residue of (±)-α-methyl-3-phenyl-7-benzofuranepropionic acid ($I_x$).

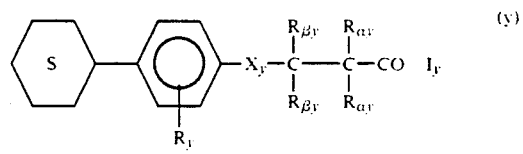 (y)

where $X_y$ is $$-\overset{O}{\underset{\|}{C}}-$$

$R_{\alpha y}$ and $R_{\beta y}$ are hydrogen or lower alkyl and $R_y$ is halo.

(The most preferred compound of formula I wherein RCO is defined by the group (y) is a compound wherein RCO is the acyl residue of 4-keto-4-(3'-chloro-4'-cyclohexyl)-phenylbutyric acid.)

Appropriate compounds of formula I are useful in the free base form, in the form of base salts where possible, and in the free acid form, or acid in the form of addition salts where possible. The three forms are within the scope of the invention. In practice, use of the salt form amounts to use of the base form. Pharmaceutically acceptable salts within the scope of the invention may be those derived from mineral acids such as hydrochloric acid and sulfuric acid; and organic acids such as ethanesulfonic acid, benzenesulfonic acid, p-toluenesulfonic acid, and the like, giving the hydrochloride, sulfamate, ethanesulfonate, benzenesulfonate, p-toluenesulfonate, and the like, respectively or those derived from bases such as suitable organic and inorganic bases. Examples of pharmaceutically acceptable base addition salts with compounds of the present invention include organic bases which are nontoxic and strong enough to form such salts. These organic bases form a class whose limits are readily understood by those skilled in the art.

Merely for purposes of illustration, the class may be said to include mono-, di-, and trialkylamines, such as methylamine, dimethylamine, and triethylamine; mono-, di-, or trihydroxyalkylamines such as mono-, di-, and triethanolamine; amino acids such as arginine, and lysine; guanidine; N-methylglucosamine; N-methylglucamine; L-glutamine; N-methylpiperazine; morpholine; ethylenediamine; N-benzylphenethylamine; tris(hydroxymethyl)aminomethane; and the like. (See for example, "Pharmaceutical Salts," *J. Pharm. Sci.*, 66(1):1-19 (1977).)

The addition salts of said basic or acidic compounds are prepared either by dissolving the free base or acid of compound I in aqueous or aqueous alcohol solution or other suitable solvents containing the appropriate acid or base reagent and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution.

The compounds of the invention may contain an asymmetric carbon atom. Thus, the invention includes the individual stereoisomers, and mixtures thereof. The individual isomers may be prepared or isolated by methods known in the art.

By virtue of their lipoxygenase inhibitory properties, said compounds and salts find application in the treatment or prophylaxis of any condition where a lipoxygenase inhibitor is indicated, especially spasmogenic and allergic conditions, psoriasis, and as utility in cytoprotection.

By virtue of their cyclooxygenase inhibitory properties, said compounds and salts find application in the treatment or prophylaxis of any condition where a cyclooxygenase inhibitor is indicated, especially pyrexia, pain, and inflammation.

By virtue of both their lipoxygenase and cyclooxygenase inhibitory properties, said compounds and salts find application in the treatment or prophylaxis of any condition where a dual lipoxygenase/cyclooxygenase inhibitor is indicated, especially any condition involving blood platelet aggregation or inflammation. In the case of inflammation, the compounds and salts are particularly suited to the treatment or prophylaxis of conditions associated with infiltration of leukocytes into inflamed tissue.

In determining when a lipoxygenase, cyclooxygenase, or dual lipoxygenase/cyclooxygenase inhibitor is indicated, of course inter alia, the particular condition in question and its severity, as well as, the age, sex, weight, and the like of the subject to be treated, must be taken into consideration and this determination is ultimately at the discretion of the attendant physician.

Examples of the aforesaid spasmogenic conditions are those involving smooth muscle tissue, especially airway smooth muscle constriction such as intrinsic asthma—(including intrinsic or idiopathic bronchial asthma and cardiac asthma), bronchitis and arterial smooth muscle constriction such as coronary spasm (including that associated with myocardial infarction, which may or may not lead to left ventricular failure resulting in cardiac asthma) and cerebral spasm or 'stroke'. Other examples include bowel disease caused by abnormal colonic muscular contraction such as may be termed 'irritable bowel syndrome', 'spastic colon', or 'mucous colitis'.

Examples of the aforesaid allergic conditions are extrinsic asthma (from which it will be appreciated that said compounds and salts are particularly favorable as antiasthmatic agents), allergic skin diseases such as eczema having a total or partial allergic origin, allergic bowel disease (including coeliac disease) and allergic eye conditions, hay fever, and allergic conjunctivitis.

Examples of the aforesaid pyretic and painful conditions include fever associated with infections, trauma and injury, malignant disease, and diseases affecting the immune system (including autoimmune diseases).

Examples of the aforesaid conditions involving blood platelet aggregation are those resulting from thrombosis, including 'stroke' having a total or partial thrombotic origin, coronary thrombosis, phlebitis, and phlebothrombosis (the latter two conditions also possibly being associated with inflammation).

Examples of the aforesaid conditions involving inflammation are inflammatory conditions of the lung, joints, eye, bowel, skin, and heart.

Inflammatory lung conditions which may be so treated and/or prevented include asthma and bronchitis (vide supra) and cystic fibrosis (which may also or alternatively involve the bowel or other tissue).

Inflammatory joint conditions which may be so treated and/or prevented include rheumatoid arthritis, rheumatoid spondylitis, osteoarthritis, gouty arthritis, and other arthritic conditions.

Inflammatory eye conditions which may be so treated and/or prevented include uveitis (including intis) and conjunctivitis (vide supra).

Inflammatory bowel conditions which may be so treated and/or prevented include Crohn's disease, ulcerative colitis, and ischemic bowel disease.

Inflammatory skin diseases which may be so treated and/or prevented include those associated with cell proliferation, such as psoriasis and eczema (vide supra) and dermatitis (whether or not of allergic origin).

Inflammatory conditions of the heart which may be so treated and/or prevented include coronary infarct damage.

Other inflammatory conditions which may be so treated and/or prevented include tissue necrosis of chronic inflammation and tissue rejection following transplant surgery.

For medical use, the amount required of a compound of formula (I) or physiologically acceptable salt thereof—(hereinafter referred to as the active ingredient) to achieve a therapeutic effect will, of course, vary both with the particular compound, the route of administration and the mammal under treatment and the particular disorder or disease concerned. A suitable dose of a compound of formula (I) or physiologically acceptable salt thereof for a mammal suffering from, or likely to suffer from any condition as described hereinbefore is 0.1 $\mu$g-500 mg of base per kilogram body weight. In the case of systemic administration, the dose may be in the range 0.5 to 500 mg of base per kilogram body weight, the most preferred dosage being 0.5 to 50 mg/kg of mammal body weight for Example 5 to 25 mg/kg; administered two or three times daily. In the case of topical administration, e.g. to the skin or eye, a suitable dose may be in the range 0.1 ng-100 $\mu$g of base per kilogram, typically about 0.1 $\mu$g/kg.

In the case of oral dosing for the treatment or prophylaxis of airway smooth muscle constriction, or asthma, or bronchitis in general, due to any course, a suitable dose of a compound of formula (I) or physiologically acceptable salt thereof, may be as specified in the preceding paragraph, but most preferably is from 1 mg to 10 mg of base per kilogram, the most preferred dosage being from 1 mg to 5 mg/kg of mammal body weight, for example from 1 to 2 mg/kg. In the case of pulmonary administration for the latter indications, the dose may be in the range of from 2 $\mu$g to 100 mg, for example from 20 $\mu$g to 0.5 mg, especially 0.1 to 0.7 mg/kg.

It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of formula (I) or a pharmacologically acceptable acid addition salt thereof and a physiologically acceptable acid addition salt thereof and a physiologically acceptable carrier therefor. Such formulations constitute a further feature of the present invention. Conveniently, the active ingredient comprises from 0.1% to 99.9% by weight of the formulation. Conveniently, unit doses of a formulation contain between 0.1 mg and 1 g of the active ingredient. For topical administration, the active ingredient preferably comprises from 1% to 2% by weight of the formulation but the active ingredient may comprise as much as 10% w/w. Formulations suitable for nasal or buccal administration, (such as self-propelling powder dispensing formulations described hereinafter), may comprise 0.1 to 20% w/w, for example 2% w/w of active ingredient.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraarticular, topical, nasal, or buccal administration.

The formulations may conveniently be presented in unit dosage form and may be prepared by any of the methods well-known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets, or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Molded tablets may be made by molding, in a suitable machine, a mixture of the powdered active ingredient and a suitable carrier moistened with an inert liquid diluent.

Formulations for rectal administration may be in the form of a suppository incorporating the active ingredient and a carrier such as cocoa butter, or in the form of an enema.

Formulations suitable for parenteral administration conveniently comprise a sterile aqueous preparation of the active ingredient which is preferably isotonic with the blood of the recipient.

Formulations suitable for intraarticular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intraarticular and ophthalmic administration.

Formulations suitable for topical administration include liquid or semi-liquid preparations such as liniments, lotions, applications, oil-in-water or water-in-oil emulsions such as creams, ointments or pastes; or solutions or suspensions such as drops. For example, for ophthalmic administration, the active ingredient may be presented in the form of aqueous eye drops as, for example, a 0.1–1.0% solution. Formulations suitable for administration to the nose or buccal cavity include powder, self-propelling and spray formulations such as aerosols and atomizers. The formulations, when dispersed, preferably have a particle size in the range of 0.1 to 200$\mu$.

A particularly valuable form of a pharmaceutical composition of the present invention, for use in the prophylaxis or treatment of airway smooth muscle constriction, or asthma or bronchitis in general, due to any cause, is one suitable for pulmonary administration via the buccal cavity. Preferably the composition is such that particles having a diameter of 0.5 to 7$\mu$, most preferably 1 to 6$\mu$, containing active ingredient, are delivered into the lungs of a patient. Such compositions are conveniently in the form of dry powders for administration from a powder inhalation device or self-propelling powder-dispensing containers, for example as a self-propelling aerosol composition in a sealed container; preferably the powders comprise particles containing active ingredient of which particles at least 98% by weight have a diameter greater than 0.5$\mu$ and at least 95% by number have a diameter less than 7$\mu$. Most desirably at least 95% by weight of the particles have a diameter greater than 1$\mu$ at least 90% by number of the particles have a diameter less than 6$\mu$.

The compositions in the form of dry powders preferably include a solid fine powder diluent such as sugar and are conveniently presented in a permeable capsule, for example of gelatin.

Self-propelling compositions of the invention may be either powder-dispensing compositions or compositions dispensing the active ingredient in the form of droplets of a solution or suspension. Self-propelling powder-dispensing compositions include a liquid propellant having a boiling point of below 65° F. at atmospheric pressure. Generally the propellant may constitute 50 to 99.9% w/w of the composition whilst the active ingredient may constitute 0.1 to 20% w/w, for example about 2% w/w of the composition. The carrier in such compositions may include other constituents, in particular a liquid nonionic or solid anionic surfactant, or a solid diluent (preferably having a particle size of the same order as of the particles of active ingredient) or both. The surfactant may constitute from 0.01 up to 20% w/w, though preferably it constitutes below 1% w/w of the composition.

Self-propelling compositions wherein the active ingredient is present in solution comprise an active ingredient, propellant, and co-solvent, and advantageously an antioxident stabilizer. The co-solvents may constitute 5 to 40% w/w of the composition, though preferably less than 20% w/w of the composition.

Compositions of the present invention may also be in the form of aqueous or dilute alcoholic solution, optionally a sterile solution, of the active ingredient for use in a nebulizer or atomizer.

Formulations of the present invention may also be in the form of an aqueous or dilute alcoholic solution, optionally a sterile solution, of the active ingredient for use in a nebulizer or atomizer, wherein an accelerated air steam is used to produce a fine mist consisting of small droplets of the solution. Such formulations usually contain a flavoring agent such as saccharin sodium and a volatile oil. A buffering agent and a surface active agent may also be included in such a formulation which should also contain a preservative such as methylhydroxybenzoate.

Other formulations suitable for nasal administration include a coarse powder having a particle size of 20 to 500 microns which is administered in the manner in which snuff is taken i.e. by rapid inhalation through the nasal passage from a container of the powder held close up to the nose.

In addition to the aforementioned ingredients, the formulations of this invention may include one or more additional ingredients such as diluents, buffers, flavoring agents, binders, surface active agents, thickeners, lubricants, preservatives e.g. methylhydroxybenzoate (including antioxidants), emulsifying agents, and the like. Any other therapeutic ingredient may comprise one or more of the following: antibiotic (e.g. antibacterial), antifungal and antiviral agents, and antihistamines (particularly peripherally acting antihistamines). However, when such other agent(s) are also present, according to another aspect of the invention, the compound of formula (I) or physiologically acceptable salt thereof and the other agent(s), need not necessarily be present as a pharmaceutical formulation as hereinbefore defined, but merely in combination or intimate admixture, i.e. optionally, a pharmaceutically acceptable carrier need not be present.

The combination with antihistamines is particularly favored for antiasthmatic use. Such an antihistamine may be selected from any compound described in European Patent Applications EP 0 859 949 A and EP 0 117 302 A. The amount and dosage regime for such an antihistamine may be chosen from any of those recited in the latter two European Specifications. Especially preferred are the antihistamines (E)-3-(6-(3-pyrrolidino)-1-(4-tolyl)prop-1E-enyl(-2-pyridyl)) acrylic acid and (E)-3-(6-(3-pyrrolidino)-1-(4-tolyl)prop-1E-enyl(-2-pyridyl))propionic acid. Another preferred antihistamine is (E)-1-(4-methylphenyl)-1-(2-pyridyl)-3-pyrrolidinoprop-1-ene. otherwise known as typrolidine.

Also preferred is the antihistamine known as Seldane.

The compound of formula I and their salts may be prepared generally by one of two of the following processes and constitute a further aspect of the present invention.

For one of the preparations of compounds of the formula I as defined above, a compound of the formula

RCOOH wherein R is as defined above;

is treated with a chloro- or bromo-generating compound, such as $SOCl_2$, $(COCl)_2$, $PBr_3$, preferably $SOCl_2$ or $(COCl)_2$ under conditions analogous to those known in the art to obtain a compound of the formula

RCOQ wherein Q is chloro or bromo and R is as defined above, and then

RCOQ is treated with a compound of the formula

or its acid addition salt in the presence of a base to give the compund of the formula I. (See Scheme I)

Where RCO is an acyl residue having s sulfinyl substituent, such as in $I_b$, or an acyl residue having the definition of the formula of $I_w$ then the preparation with treatment by a chloro- or bromo- generating compound, such as $SOCl_2$, $(COCl)_2$, or $PBr_3$ described above does not provide a desired product. For this definition of RCO, an alternate preparation is thus required.

That is, surprisingly, for compounds having RCO defined by $I_b$ having a sulfoxide group among the definitions of its substituents, the sulfoxide reacts with the chloro- or bromo- of the generating compound so a product of the formula I having the sulfoxide as a substituent cannot be obtained. In other words, the acyl residue of sulindac does not provide the $RCON(OR_1)R_2$ desired by use of the above desired procedure.

Further, in like manner, the compounds having the formula RCO of the structure $I_w$ cannot be treated with a chloro- or bromo- generating compound, such as $SOCl_2$, $(COCl)_2$, or $PBr_3$ to obtain the desired product of the above preparation because an intramolecular cyclization to oxindole occurs. For example, the acyl residue of methyl diclofenate as shown in U.S. Pat. No. 4,092,430 cannot be treated as described in the above preparation and reacted with the substituted hydroxyamine hydrogen chloride of the present invention contrary to the teaching of U.S. Pat. No. 4,092,430.

Therefore, in these two instances use of the alternate preparation described hereinafter is critical.

In an alternate preparation of the compound of the formula I as defined above a compound of the formula

RCOOH is treated with a coupling agent, such as 1,1'-carbonyldiimidazole, N-ethoxycarbonyl-2-ethoxy-1,3-dihydroquinoline, dicyclohexylcarbodiimide, dicyclohexylcarbodiimide/hydroxybenzenetriazole or the like, preferably 1,1'-carbonyldiimidazole; and then further treated with a compound of the formula

or the acid addition salt thereof; wherein $R_1$ and $R_2$ are as defined above; to obtain the compound of formula I. (See Scheme II)

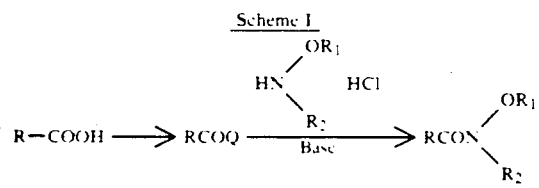

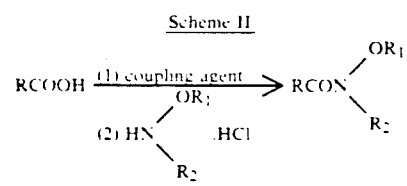

The reactions of Scheme II are carried out in organic solvents such as methylene chloride, DMF, THF and the like, preferably in methylene chloride.

The hydroxamic acid formation is carried out at a temperature ranging from about 0° C. to about 50° C., preferably at about room temperature.

One of skill in the art would recognize variations in the sequence and would recognize appropriate reaction conditions from analogous reactions which may be appropriately used in the processes to make the compounds of formula (I) herein. Further, the starting materials are known or can be prepared by known methods.

Under certain circumstances it is necessary to protect either the N or O of intermediates in the above noted process with suitable protecting groups which are known. Introduction and removal of such suitable oxygen and nitrogen protecting groups are well-known in the art of organic chemistry; see for example "Protective Groups in Organic Synthesis," T. W. Greene, (Wiley-Interscience), New York, 1981.

Examples of suitable oxygen protecting groups are benzyl, t-butyldimethylsilyl, ethoxyethyl, and the like. Protection of an N-H containing moiety is necessary for some of the processes described herein for the preparation of compounds of this invention. Suitable nitrogen protecting groups are benzyl, triphenylmethyl, trialkylsilyl, trichloroethylcarbamate, trichloroethoxycarbonyl, vinyloxycarbamate, and the like.

Under certain circumstances it is necessary to protect two different oxygens with dissimilar protecting groups such that one can be selectively removed while leaving the other in place. The benzyl and t-butyldimethylsilyl groups are used in this way; either is removable in the presence of the other, benzyl being removed by catalytic hydrogenolysis, and t-butyldimethylsilyl being removed by reaction with, for example, tetra-n-butylammonium fluoride.

In the process described herein for the preparation of compounds of this invention the requirements for protective groups are generally well recognized by one skilled in the art of organic chemistry, and accordingly the use of appropriate protecting groups is necessarily implied by the processes of the charts herein, although not expressly illustrated.

The products of the reactions described herein are isolated by conventional means such as extraction, column chromatography, flash chromatography, and the like.

The salts of the compounds of formula (I) described above are prepared by reacting the appropriate base or acid with a stoichiometric equivalent of the compounds of formula (I), respectively, to obtain pharmaceutically acceptable salts thereof.

The invention is further elaborated by the representative examples as follows. Such examples are not meant to be limiting.

EXAMPLES

Example 1

(Z)-6-fluoro-N-hydroxy-N,2-dimethyl-3-[[4-(methylsulfinyl)phenyl]methylene]-3H-indene-1-acetamide.

A mixture of (Z)-5-fluoro-2-methyl-1-[[4(methylsulfinyl)phenyl]methylene]-1H-indene-3-acetic acid (sulindac, Sigma) (7.13 g, 0.02 mole) and 1,1'-carbonyldiimidazole (4.9 g, 0.03 mole) in methylene chloride (200 ml) is stirred at room temperature for 30 minutes, then N-methyl-hydroxylamine hydrochloride (3.34 g, 0.04 mole) is added. After being stirred an additional 41 hours, the mixture is poured into cold 2 normal hydrochloric acid (1 l) and extracted with methylene chloride (400 ml). The organic solution is washed successively with 2 normal hydrochloric acid (1 l), water (3×1 l) and is dried over sodium sulfate. The solvent is removed under reduced pressure and the residue (8.2 g) is chromatographed on silica gel (225 g). Elution with 95:5 mixture of chloroform and methanol, gives 7.35 g of a solid. Recrystallization from ethyl acetate-hexane, then from methylene chloride-hexane, gives 5.5 g (75.3%) of analytically pure (Z)-6-fluoro-N-hydroxy-N,2-dimethyl-3-[[4-(methylsulfinyl)phenyl]methylene]-3H-indene-1-acetamide, m.p. 156°-160° C.

Example 2

(Z)-6-fluoro-N-methoxy-2-methyl-3-[[4-(methylsulfinyl) phenyl]methylene]-3H-indene-1-acetamide.

Prepared by the method described in Example 1, using appropriate starting materials. Recrystallization from methanol-ethyl acetate-hexane, gives analytically pure (Z)-6-fluoro-N-methoxy-2-methyl-3-[[4-(methylsulfinyl) phenyl]methylene]-3H-indene-1-acetamide in 50.8% yield, m.p. 177°-179° C.

Example 2A (Z)-6-fluoro-N-hydroxy-2-methyl-3-[[4-(methylsulfinyl) phenyl]methylene]-3H-indene-1-acetamide.

Prepared by the method described in Example 1, using appropriate starting materials. Recrystallization from methanol/ethyl acetate/hexane gives analytically pure (Z)-6-fluoro-N-hydroxy-2-methyl-3-[[4-(methylsulfinyl) phenyl]-methylene]-3H-indene-1-acetamide 28.9% yield, m.p. 208°-209° C. dec.

Example 2B (Z)-6-Fluoro-N-hydroxy-N-(1-methylethyl)-2-methyl-3-[[4-(methylsulfinyl)phenyl]methylene]-3H-indene-1-acetamide.

Prepared by the method described in Example 2, using appropriate starting materials. The crude product is flash chromatographed over silica gel using 5% CH₃OH—CHCl₃ as eluent and obtained the pure analytical product as viscous oil in 94.8% yield.

Example 3

1-(4-Chlorobenzoyl)-N-hydroxy-5-methoxy-N,2-dimethyl-1H-indole-3-acetamide.

Oxalyl chloride (56.92 g, 0.448 mole) is added dropwise over 20 minutes with stirring to a solution of 1(p-chlorobenzoyl)-5-methoxy-2-methylindole-3-acetic acid (indomethacin, sigma) (64.2 g, 0.179 mole) in methylene chloride (500 ml) and dimethylformamide (13.12 g, 0.179 mole) at $< -2°$ C. After being stirred for 80 minutes, this solution is added to a solution of N-methylhydroxylamine hydrochloride (59.9 g, 0.717 mole) and triethylamine (163.3 g, 1.61 mole) in tetrahydrofuran (200 ml) and water (100 ml). After being stirred for an additional 75 minutes, the mixture is poured into cold 2 normal hydrochloric acid (3 l) and extracted with methylene chloride (1.5 l). The organic layer is washed with water and dried over sodium sulfate. The solvent is removed under reduced pressure and the residue (68.7 g) is chromatographed on 663 g of silica gel. Elution with chloroform, then with 95:5 mixture of chloroform-methanol gives 63.1 g of a solid. Recrystallization from methanol, gives 55.49 g (80%) of analytically pure 1-(4-chlorobenzoyl)-N-hydroxy-5-methoxy-N,2-dimethyl-1H-indole-3-acetamide, m.p. 170°–171° C.

Example 4

1-(4-Chlorobenzoyl)-N,5-dimethoxy-2-methyl-1H-indole-3acetamide.

Prepared by the method described in Example 3 using appropriate starting materials. Recrystallization from methanol, gives analytically pure 1-(4-chlorobenzoyl)-N,5-dimethoxy-2-methyl-1H-indole-3-acetamide in 73.7% yield, m.p. 184°–185° C.

Example 5

1-(4-Chlorobenzoyl)-N-hydroxy-5-methoxy-2-methyl-N-(1-methylethyl)-1H-indole-3-acetamide.

Prepared by the method described in Example 3 using appropriate starting materials. The crude product is chromatographed over silica gel using chloroform as eluent. Recrystallization from methanol gives analytically pure 1-(4-chlorobenzoyl)-N-hydroxy-5-methoxy-2-methyl-N-(1-methylethyl)-1H-indole-3-acetamide in 41.6% yield, m.p. 198°–199° C.

Example 6

1-(4-Chlorobenzoyl)-N-cyclohexyl-N-hydroxy-5-methoxy-2-methyl-1H-indole-3-acetamide.

Prepared by the method described in Example 3 using appropriate starting materials. The crude product is chromatographed on silica gel using chloroform as eluent. Recrystallization from methanol gives analytically pure 1-(4-chlorobenzoyl)-N-cyclohexyl-N-hydroxy-5-methoxy-2-methyl-1H-indole-3-acetamide in 49.2% yield, m.p. 208°–210° C.

Example 6A 1-(4-Chlorobenzoyl)-N,5-dimethoxy-N,2-dimethyl-1H-indole-3-acetamide.

Prepared by the method described in Example 3 using appropriate starting materials. The crude product is flash chromatographed over silica gel using CHCl₃ as eluent. Recrystallization from CH₂Cl₂-isoPr₂O gives analytically pure product in 86.5% yield, m.p. 155°–157° C.

Example 6B 1-(4-Chlorobenzoyl)-N-hydroxy-5-methoxy-2-methyl-N-phenyl-1H-indole-3-acetamide.

Prepared by the method described in Example 3 using appropriate starting materials. The crude product is flash chromatographed over silica gel using CHCl₃ as eluent. Recrystallization of the purified product from methanol gives analytically pure product in 11.4% yield, m.p. 173°–174° C.

Example 6C 1-(4-Chlorobenzoyl)-N-benzyl-N-hydroxy-5-methoxy-2-methyl-1H-indole-3-acetamide.

Prepared by the method described in Example 3 using appropriate starting materials. The crude product is flash chromatographed over silica gel using 5% CH₃OH—CH₂Cl₂ as eluent. Recrystallization of the purified product from ethylacetate-ether gives analytically pure product in 27.6% yield, m.p. 188°–189° C.

Example 7

N-Methoxy-2-[(2,6-dichlorophenyl)amino]-benzeneacetamide.

A warm solution of 2-[(2,6-dichlorophenyl)amino]-benzeneacetic acid (2.03 g; 7 mmol) in CH₂Cl₂ (100 mL) is treated with 1,1'-carbonyl-diimidazole (1.75 g; 11 mmol) and the mixture is stirred at room temperature for 5.0 minutes when a clear solution is obtained. The solution is then treated with methoxylamine hydrochloride (1.50 g; 18 mmol) and the reaction mixture stirred at room temperature for 108 hours. It is then decomposed with water, extracted with CH₂Cl₂, dried over Na₂SO₄ and then evaporated to dryness to give a solid. Fractional recrystallization of the crude product from a mixture of toluene-CH₂Cl₂ gives off-white crystalline solid (1.27 g; 55.8%); mp 177°–178° C.

Example 8

N-Hydroxy-N-methyl-2-[(2,6-dichlorophenyl)amino]-benzeneacetamide.

1,1'-Carbonyl-diimidazole (5.5 g; 34 mmol) is slowly added to a warm solution of 2-[(2,6-dichlorophenyl)-amino]-benzeneacetic acid (6.5 g; 22 mmol) in CH₂Cl₂ (600 mL) and stirred at room temperature for 2.0 hours when a clear solution is formed. N-Methylhydroxylamine hydrochloride (5.5 g; 66 mmol) is slowly added to the solution and the mixture stirred at room temperature for 48 hours. It is decomposed with water, extracted with CH₂Cl₂ and dried over Na₂SO₄. The solvent is evaporated off and the residue flash chromatographed over silica gel (250 g) using 10% EtOH-CH₂Cl₂ as eluant to give the pure product as white solid which is recrystallized from toluene-$CH_2Cl_2$. Yield 2.95 g (41.2%); mp 135°-138° C.

The usefulness of the compounds of the present invention as inhibitors of the 5-lipoxygenase enzyme, cyclooxygenase, or other related biochemical actions may be demonstrated by their effectiveness in various standard test procedures. A description of each procedure follows.

ARBL/ARBC Whole Cell 5-Lipoxygenase and Cyclooxygenase Assays

Materials

The rat basophilic leukemia cell line (RBL-1) was obtained from the American Type Culture Collection (Rockville, Md.).

Radioimmuno assay (RIA) kits of $LTB_4$ and $PGF_{2\alpha}$ were obtained from Amersham (Arlington Heights, Ill.) and Seragen (Boston, Mass.) respectively.

All tissue culture media were obtained from GIBCO (Grand Island, N.Y.).

Method

RBL-1 cells are grown in suspension culture in Eagle's minimum essential medium supplemented with 12% fetal bovine serum at 37° C. in an incubator supplied with air-5% carbon dioxide. Cells are harvested by centrifugation. They are washed with cold phosphate buffered saline pH 7.4 (PBS; NaCl, 7.1 g; $Na_2HPO_4$, 1.15 g; $KH_2PO_4$, 0.2 g; and KCl, 0.2 g/l). Cells are finally suspended in PBS containing 1.0 mM calcium at a density of $2 \cdot 10^6$ cells/ml. Cells are incubated with and without test agent (in DMSO) (1% DMSO is without effect on arachidonic acid metabolism) for ten minutes at room temperature. Calcium ionophore A23187 (5 μM) is added and cells are incubated for seven minutes at 37° C. The reaction is stopped by chilling the tubes on ice for ten minutes. Cells are separated by centrifugation and the supernatant is stored at −20°. Aliquots (100 μl) are analyzed for $LTB_4$ and $PGF_{2\alpha}$ using radioimmuno assay kits as provided by the supplier.

Table 1 contains biochemical data obtained from this whole cell assay as $IC_{50}s$ which are calculated as the amount of test compound causing 50% inhibition of $LTB_4$ or $PGF_{2\alpha}$ formation.

Carrageenan-Induced Rat Foot Paw Edema-2 (CFE-2) Assay

Protocol

Carrageenan solution (1% w/v) is prepared by dissolving 100 mg carrageenan (Marine Colloidal Div., Springfield, N.J.) in 10 ml of sterile saline (0.9%) solution (Travenol). The solution is vortexed for thirty to forty-five minutes. Animals are dosed with compound one hour before carrageenan challenge. Foot paw edema is induced by injecting 0.05 ml of the 1% carrageenan subcutaneously into the plantar portion of the right hind paw of each rat under light anesthesia. Initial foot paw volume is measured immediately following carrageenan challenge using mercury plethysmography (Buxco Electronics). Edema is measured five hours after carrageenan. The difference between the five-hour and the initial paw volume is expressed as delta edema. The delta edema for each test group of animals is used to calculate the percent inhibition of edema achieved by the compound at the test dose compared with the vehicle control group. The $ID_{25}$ (the dose at which swelling is inhibited by 25%) was calculated by probit analysis for the dose at which a result of 25 percent inhibition occurs.

Mycobacterium—Induced Rat Footpad Edema Assay (MFE)

Protocol

*Myobacterium butyricum* (5 mg/ml) is suspended in paraffin oil by sonication for ten minutes in an ice bath. Footpad edema is induced on Day 0 by injecting 0.1 ml of the Mycobacterium mixture into the left hindpaw of lightly anesthetized rats. Swelling in the injected hindpaw is determined by mercury plethysmography seventy-two hours after injection. Groups of rats are treated with test compounds (suspended in 0.5% hydroxypropyl methylcellulose with 0.2% Tween-80) or vehicle one hour before Myobacterium injection and on Days 1 and 2. Inhibition of swelling is determined by comparing the change in hindpaw volume in compound- and vehicle-treated rats. An $ID_{40}$ (the dose at which swelling is inhibited by 40%) was calculated by probit analysis.

Gastric Ulcerogenicity (UD)

Protocol

Male outbred Wistar rats (100-250 gms) were fasted for twenty-four hours. After fasting, test compounds were administered orally (in 2 ml/Kg of 0.5% hydroxypropyl methylcellulose) and the rats were denied access to food and water for six more hours. The rats were then sacrificed with $CO_2$ so that the stomachs could be removed, opened along the greater curvature, and evaluated for the presence of gastric ulcers. Results are expressed as the percent of rats with gastric ulcers at a given dose.

The results of the CFE-2, MFE, and UD assays for each of the noted compounds is shown in the following Table 1 and Table 2.

TABLE I

| | | SULINDAC SERIES | | | |
|---|---|---|---|---|---|
| PD # | X | $ARBC^a/ARBL^b$ | $RATIO^c$ | $CFE^d$ | $MFE^e$ |
| SULINDAC | | | | | |
| Example 1 | CON(ME)OH | 0% @ 32*/1.0 | — | 15% @ 30 | 30% @ 10 |
| Example 2 | CONHOME | 0% @ 32*/26.4 | — | — | — |
| Example 2A | CONHOH | 0% @ 32*/12.9 | — | 31% @ 30 | 53% @ 50 |

*Parent sulindac sulfoxides are not CO inhibitors, but converted to CO Inhibitory sulfides in vivo
[a] ARBC = RBL Whole Cell Cyclooxygenase Assay, IC50 (μM) for $PGF_{2\alpha}$ inhibition.
[b] ARBI = RBL Whole Cell 5-Lipoxygenase Assy, IC50 (μM) for $LTB_4$ inhibition
[c] RATIO = Selectivity of Inhibition. If > 1.0 compound is cyclooxygenase selective. If < 1.0 compound is 5-lipoxygenase selective
[d] CFE = Carrageenan Footpad Edema Model, ID25 or % Inhibition @ Dose (mg/kg PO)
[e] MFE = Mycobacterium Footpad Edema Model, ID40 or % Inhibition @ Dose (mg/kg PO)

TABLE 2

| Example # | X | INDOMETHACIN SERIES | | | | | |
|---|---|---|---|---|---|---|---|
| | | ARBC[a] | ARBL[b] | RATIO[c] | CFE[d] | MFE[e] | UD50[f] |
| Indomethacin | OH | 0.5 | >100 | >200 | 36% @ 5 | 0.21 | 5.4 |
| Oxametacin | NHOH | 1.1 | 7.5 | 6.8 | 46% @ 30 | | 103 |
| Example 3 | NMEOH | 5.2 | 1.4 | 0.27 | 29% @ 10 | <2 | 10% @ 100 |
| Example 4 | NHOME | 0.2 | 24 | 120 | 40% @ 10 | | 42 |
| Example 5 | N(iPR)OH | 2.7 | 0.9 | 0.33 | 27% @ 10 | 0.82 | N @ 100 |
| Example 6 | N(C—C6H11)OH | 0.1 | 1.6 | 16.0 | 22% @ 10 | 4.7 | N @ 200 |

[a] ARBC = RBL Whole Cell Cyclooxygenase Assay IC50 (μM)
[b] ARBL = RBL Whole Cell 5-Lipoxygenase Assay IC50 (μM)
[c] RATIO = Selectivity of Inhibition. If > 1.0 compound is cyclooxygenase selective. If < 1.0 compound is 5-lipoxygenase selective
[d] CFE = Carrageenan Footpad Edema Model. ID25 or % Inhibition @ Dose (mg/kg PO)
[e] MFE = Mycobacterium Footpad Edema Model. ID50 or % Inhibition @ Dose (mg/kg PO)
[f] UD50 = Dose (mg/kg PO) causing ulcers in 50% of animals Accordingly, the present invention is
(a) a compound of formula I or an acid addition salt thereof;
(b) a method for preparing a compound of formula I or a pharmacologically acceptable acid addition salt thereof;
(c) a pharmaceutical formulation comprising a compound of formula (I) or a physiologically acceptable salt thereof and a pharmaceutically acceptable carrier therefor;
(d) a method for preparing such formulations;
(e) a method for the inhibition of the lipoxygenase and/or cyclooxygenase pathways of the arachidonic acid metabolism by use of a nontoxic, effective, inhibitory amount of a compound of formula I or a physiologically acceptable salt thereof;
(f) a method for the prophylaxis or treatment of disease or condition in a mammal, including man, comprising the administration to said mammal of a nontoxic, therapeutically or prophylactically effective amount of a compound of formula I or a physiologically acceptable salt thereof;
(g) a method for the prophylaxis or treatment of any individual condition described herein, in a mammal, including man, comprising the administration to said mammal of a nontoxic therapeutically or prophylactically effective amount of a compound of formula I or a physiologically acceptable salt thereof;
(h) a method for the prophylaxis or treatment of inflammation, arthritis, pain or fever in a mammal, including man, comprising the administration to said mammal of a nontoxic, effective, antiinflammation, antiarthritic, analgesic, antipyretic amount of a compound of formula I or a physiologically acceptable salt thereof;
(i) a method for the prophylaxis or treatment of asthma in a mammal, including man, comprising administration to said mammal of a nontoxic, effective, antiasthmatic amount of a compound of formula I or a physiologically acceptable salt thereof;
(j) a compound of formula I or a physiologically acceptable salt thereof for use in medicine, especially as defined in (f)–(h) above;
(k) use of a compound of formula I or a physiologically acceptable salt thereof in the manufacture of medical therapeutic agents, particularly those for use as defined in (f)–(k) above; and
(l) any novel feature described herein.

We claim:
1. A compound of the formula

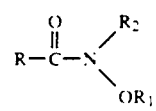

or a pharmaceutically acceptable acid addition or base salt thereof wherein
i) RCO is

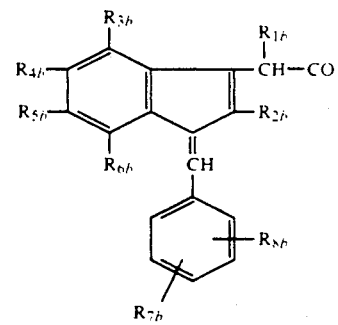

wherein:
$R_{1b}$ is hydrogen, lower alkyl or halogenated lower alkyl;
$R_{2b}$ is hydrogen or alkyl;
$R_{3b}$, $R_{4b}$, $R_{5b}$ and $R_{6b}$ each are hydrogen, lower alkyl, lower alkoxy, nitro, amino, lower alkylamino, lower dialkylamino, lower dialkylamino lower alkyl, sulfamyl, lower alkylthio, mercapto, hydroxy, hydroxy lower alkyl, lower alkylsulfonyl, halogen, carboxyl, carbo-lower alkoxy, carbamido, halogenoalkyl, cycloalkyl, or cycloalkoxy;
$R_{7b}$ is lower alkylthio, alkylsulfinyl or alkylsulfonyl;
$R_{8b}$ is hydrogen, halogen, hydroxy, alkoxy or haloalkyl;
ii) $R_1$ is hydrogen, lower alkyl or acyl;
iii) $R_2$ is H, lower alkyl, cycloalkyl having a ring of from three to seven carbons which ring is optionally substituted by lower alkyl of from one to five carbons, aryl, arylalkyl or heteroaryl which is pyrrolyl, furanyl, thienyl, pyridinyl, imidazolyl, pyrazinyl, or thioazolyl.

2. A compound of claim 1 which is (Z)-6-fluoro-N-hydroxy-N,2-dimethyl-3-[[4-(methylsulfinyl)phenyl]methylene]-3H-indene-1-acetamide.

3. A compound of claim 1 which is (Z)-6-fluoro-N-methoxy-2-methyl-3-[[4-(methylsulfinyl)phenyl]methylene]-3H-indene-1-acetamide.

4. A compound of claim 1 which is (Z)-6-fluoro-N-hydroxy-2-methyl-3-[[4-(methylsulfinyl)phenyl]methylene]-3H-indene-1-acetamide.

5. A compound of claim 1 which is (Z)-6-fluoro-N-hydroxy-N-(1-methylethyl)-2-methyl-3-[[4-(methylsulfinyl)phenyl]methylene]-3H-indene-1-acetamide.

6. A pharmaceutical composition comprising an effective amount of a compound of the formula I of claim 1 together with a pharmaceutically acceptable carrier.

7. The method of treating a condition advantageously affected by inhibition of 5-lipoxygenase, cyclooxygenase, or both comprising administering a compound of the formula I of claim 1 in unit dosage form.

* * * * *